Figure 3:
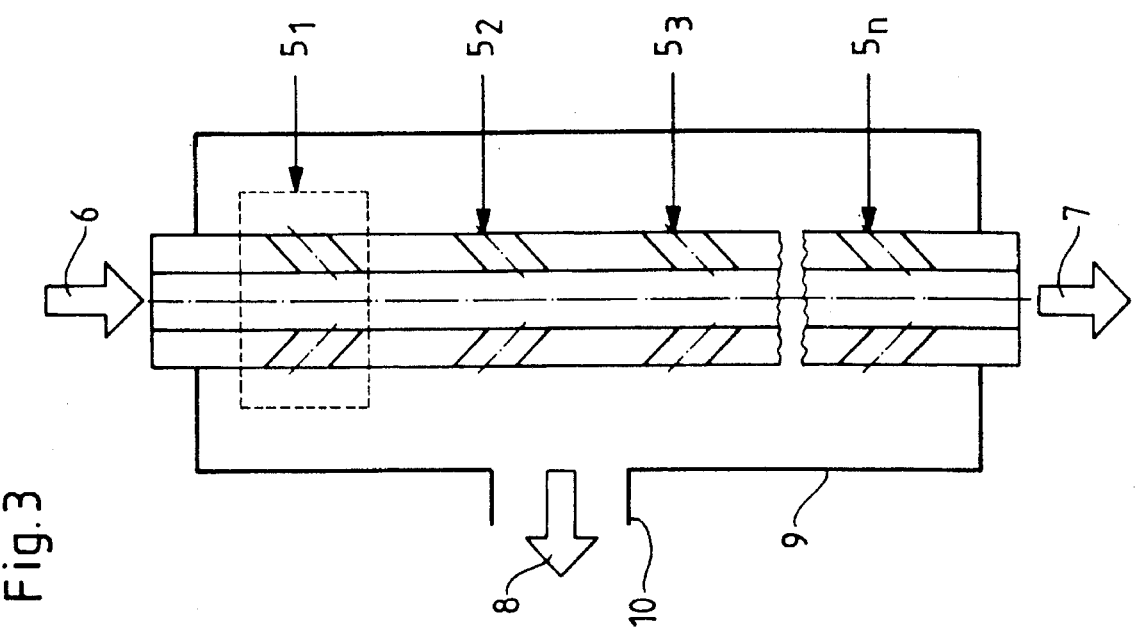

United States Patent [19]

Koglin

[11] Patent Number: 5,618,444
[45] Date of Patent: Apr. 8, 1997

[54] METHOD FOR SEPARATING A DISPERSION OF PARTICLES IN LIQUIDS INTO A PARTICLE-ENRICHED AND A PARTICLE-DEPLETED PARTIAL STREAM

[75] Inventor: Bernd Koglin, Bergisch Gladbach, Germany

[73] Assignee: Bayer Aktiengesellschaft, Leverkusen, Germany

[21] Appl. No.: 666,998

[22] Filed: Jun. 21, 1996

Related U.S. Application Data

[63] Continuation of Ser. No. 294,226, Aug. 22, 1994, abandoned.

[30] Foreign Application Priority Data

Aug. 27, 1993 [DE] Germany ............... 43 28 885.5

[51] Int. Cl.$^6$ ................................. B01D 37/00
[52] U.S. Cl. ............................. 210/767; 210/542
[58] Field of Search ................. 210/767, 801, 210/802, 808, 542, 320, 433.1

[56] References Cited

U.S. PATENT DOCUMENTS

| | | |
|---|---|---|
| 1,519,428 | 12/1924 | Wilisch . |
| 2,152,115 | 3/1939 | Van Tongeren . |
| 2,289,474 | 7/1942 | Anderson . |
| 3,279,155 | 10/1966 | Lambert . |
| 3,725,271 | 4/1973 | Giannotti ............... 210/767 |
| 5,004,484 | 4/1991 | Stirling et al. ............... 210/767 |
| 5,441,638 | 8/1995 | Tillich ............... 210/320 |

FOREIGN PATENT DOCUMENTS

| | | |
|---|---|---|
| 2300580 | 11/1974 | Germany . |
| 3519620 | 1/1986 | Germany . |
| 3632226 | 4/1987 | Germany . |
| 4218379 | 9/1993 | Germany . |
| 1386651 | 1/1986 | U.S.S.R. . |
| 1551726 | 3/1990 | U.S.S.R. . |
| 2055302 | 3/1981 | United Kingdom ............... 210/320 |

*Primary Examiner*—Robert J. Popovics
*Attorney, Agent, or Firm*—Sprung Horn Kramer & Woods

[57] ABSTRACT

The methods consists in that the suspension is made to flow as the feed stream through a narrow channel or a capillary and partial streams are drawn off from the wall on the periphery of the channel and/or the capillary through openings in the channel wall and/or capillary wall, the cross-section of which is larger than the mean particle cross-section (median value), the particle concentration being enriched in the main stream and diluted in the partial streams compared to the feed stream. The device consists in that several holes and/or (in the case of a channel) two gaps are arranged evenly distributed over the periphery of a pipe or channel in which the main stream is conveyed. The diameter of the holes is between 10% and 90% of the pipe diameter and the gap width between 10% and 30% of the channel width.

14 Claims, 4 Drawing Sheets

METHOD FOR SEPARATING A DISPERSION OF PARTICLES IN LIQUIDS INTO A PARTICLE-ENRICHED AND A PARTICLE-DEPLETED PARTIAL STREAM

This application is a continuation of application Ser. No. 08/294,226, filed on Aug. 22, 1994 which is now abandoned.

The invention relates to a method with which a flowing dispersion of particles in a liquid is continuously broken down into a particle-enriched and a particle-depleted partial stream.

Various devices and methods by which to solve this task are known. They include sedimentation under gravity and in centrifuges, various filtration methods, flotation and specific separation methods which employ electric or magnetic fields for example.

Reference is made in particular to the following known continuous flow separation methods.

In the hydrocyclone, separation takes place on the basis of centrifugal force. This is generated by a turbulent flow which is generated by the tangential inflow of the dispersion into a pipe. The particle-depleted liquid can be drawn off in the center of the pipe whilst the particle-enriched dispersion at the pipe casing is removed via a superimposed axial flow. Because of its separation principle the hydrocyclone is only suitable for particles whose density differs substantially from that of the liquid. Even with density differences of a few g/cm$^3$, adequate separation effects are only produced for particle sizes above approx. 5 μm.

In cross-flow filtration the dispersion flows through a pipe with a porous wall, for example. With the aid of an excess pressure liquid is simultaneously pressed through the porous wall, a diaphragm for example. If the particles are retained by the porous wall the permeate liquid is clear. The cross-flow flow prevents or restricts the formation of filter cake on the internal wall of the pipe so that a particle-enriched dispersion is carried out with the core stream. It is essential to cross-flow filtration that the pores of the diaphragm are finer than the particles of the dispersion. Diaphragms with very fine pores, which can retain virtually any fine particles, are available. The disadvantage is, however, that the throughflow resistance and the risk of blockage increase sharply, the finer the pores. Deformable particles in particular block the diaphragm and form a dense layer of filter cake which is virtually impermeable to liquid and which cannot be completely removed even by means of cross-flow.

The object of the invention is to develop as simple a method as possible and a device for the concentration of suspensions which produces good results, i.e. a high degree of particle separation with adequate throughput, both in the case of imperceptible density difference of the particles, when sedimentation methods fail, and in the case of fine deformable particles with which cake or cross-flow filtration methods fail.

According to the invention this object is achieved in that the suspension to be concentrated is made to flow as the feed stream through a narrow channel or a capillary and partial streams are drawn off from the wall on the periphery of the channel and/or the capillary through openings in the channel wall and/or capillary wall, the cross-section of which is larger than the mean particle cross-section (median value), the particle concentration being enriched in the main stream and diluted in the partial streams compared to the feed stream. A narrow channel is to be understood as a channel of any cross-section including circular (capillary) and rectangular cross-sections. In this case a "narrow" channel or a "narrow" capillary are intended to mean channels with a gap width or capillaries with a diameter of 0.5 μm to 10 mm, preferably 10 μm to 10 mm.

The invention makes use of a new effect which is not based on the principle of centrifugal force or on that of filtration. Rather, the effect is based on the particle concentration in a stream which declines in the proximity of the wall. For this reason the method according to the invention is designated below as "stream concentration" and the separating element according to the invention as "stream concentrator". In particularly favorable cases not only a concentration but a complete separation of the particles can be achieved.

Preferably the partial streams close to the wall are drawn off with a direction component against the main stream, the deviation angle advantageously being between 120° and 150°.

Furthermore the method is appropriately implemented in such a way that turbulent flow conditions prevail in the main stream and laminar flow conditions in the partial streams.

According to a preferred embodiment the flow ratios are set in such a way that the partial stream from the openings at identical axial height is 2% to 10%, preferably 4% to 7%, of the main stream.

Particularly high degrees of separation can be achieved when partial streams are drawn off successively in the form of a cascade viewed in the direction of flow.

The method is preferably implemented in such a way that the sum of all partial streams is up to 99% of the feed stream.

The method can also be used advantageously to grade particles of different size. For this purpose the partial streams drawn off from different axial heights are discharged separately in order to obtain partial streams with different particle concentration and different particle size distribution.

A further development of the method according to the invention consists in that the stream concentrator is integrated into a chemical reaction process in which a dispersion is obtained, the particles and the liquid being separated from each other in the course of the on-going chemical reaction.

According to the invention a device suitable for implementing the stream concentration comprises a pipe in which the main stream is conveyed, on the periphery of which several, preferably 3 to 6 holes with diameters between 10% and 90%, particularly preferably between 40% and 70% of the channel diameter are arranged evenly distributed at identical axial height.

Alternatively a device can also be used which according to the invention comprises a flat channel with rectangular cross-section, in which the main stream is conveyed and which has, on opposite walls at identical axial height, two gaps with gap widths between 5% and 50%, preferably between 10% and 30% of the channel width.

The holes or gaps for drawing off the particle-depleted partial streams are preferably dimensioned in such a way that their inside width is 1 to 10 times, preferably 2 to 5 times the median value of the particle size distribution of the feed stream.

Advantageously, several, preferably 20 to 40 such hole and/or gap systems are connected behind each other in the form of a cascade viewed in the direction of flow. The stream concentrator is appropriately dimensioned in such a way that the total cross-section of the openings at identical axial height is 0.5 to 4 times, preferably 1 to 2 times the channel and/or capillary cross-section.

Figure 1:
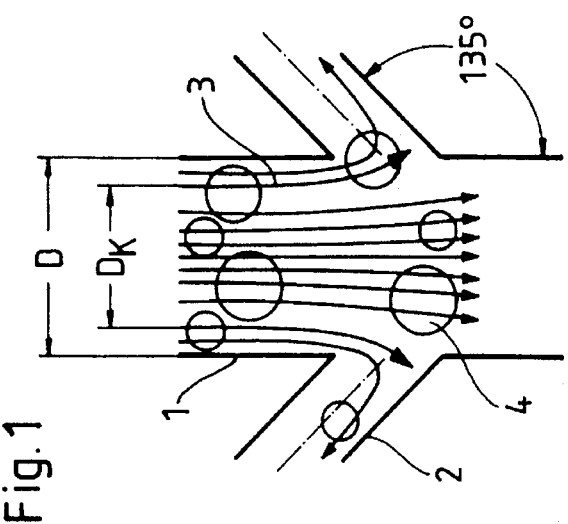
Figure 2:
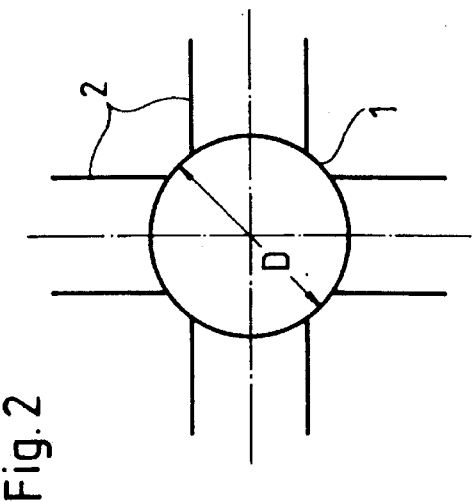
Figure 4:
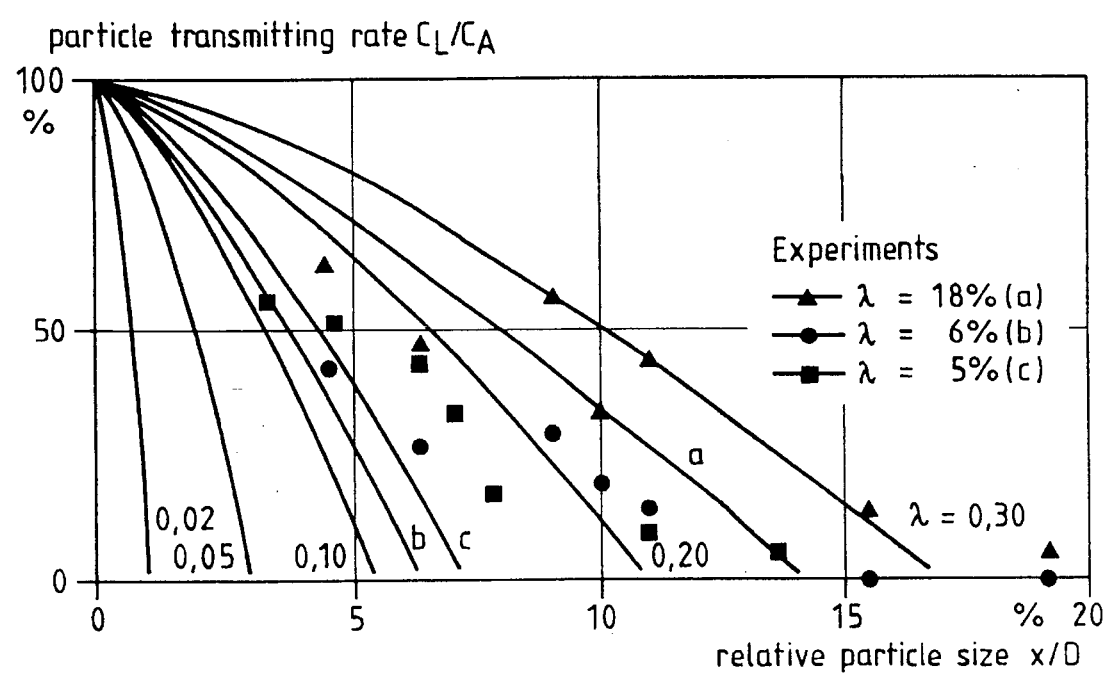
Figure 5:
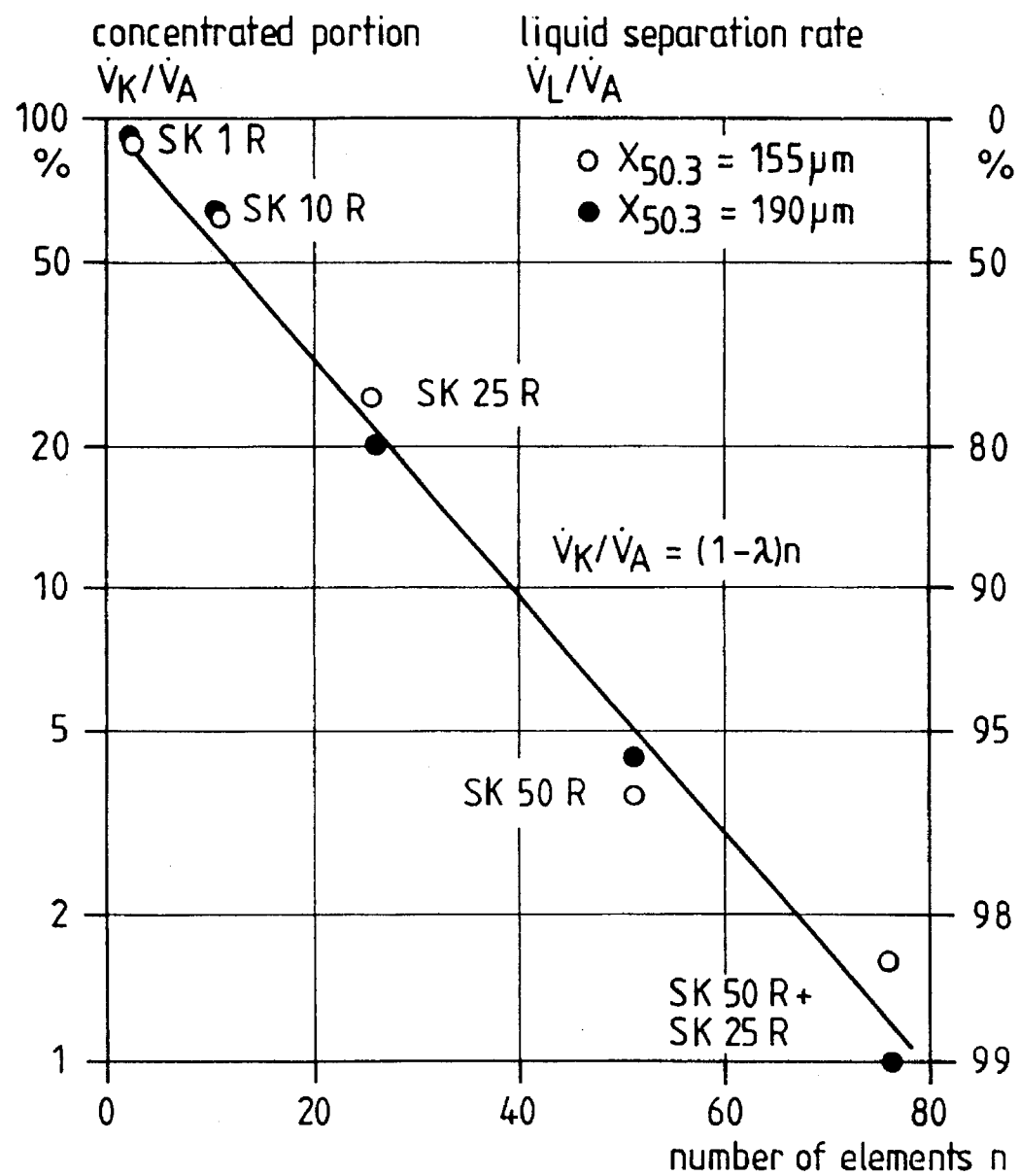
Figure 6:
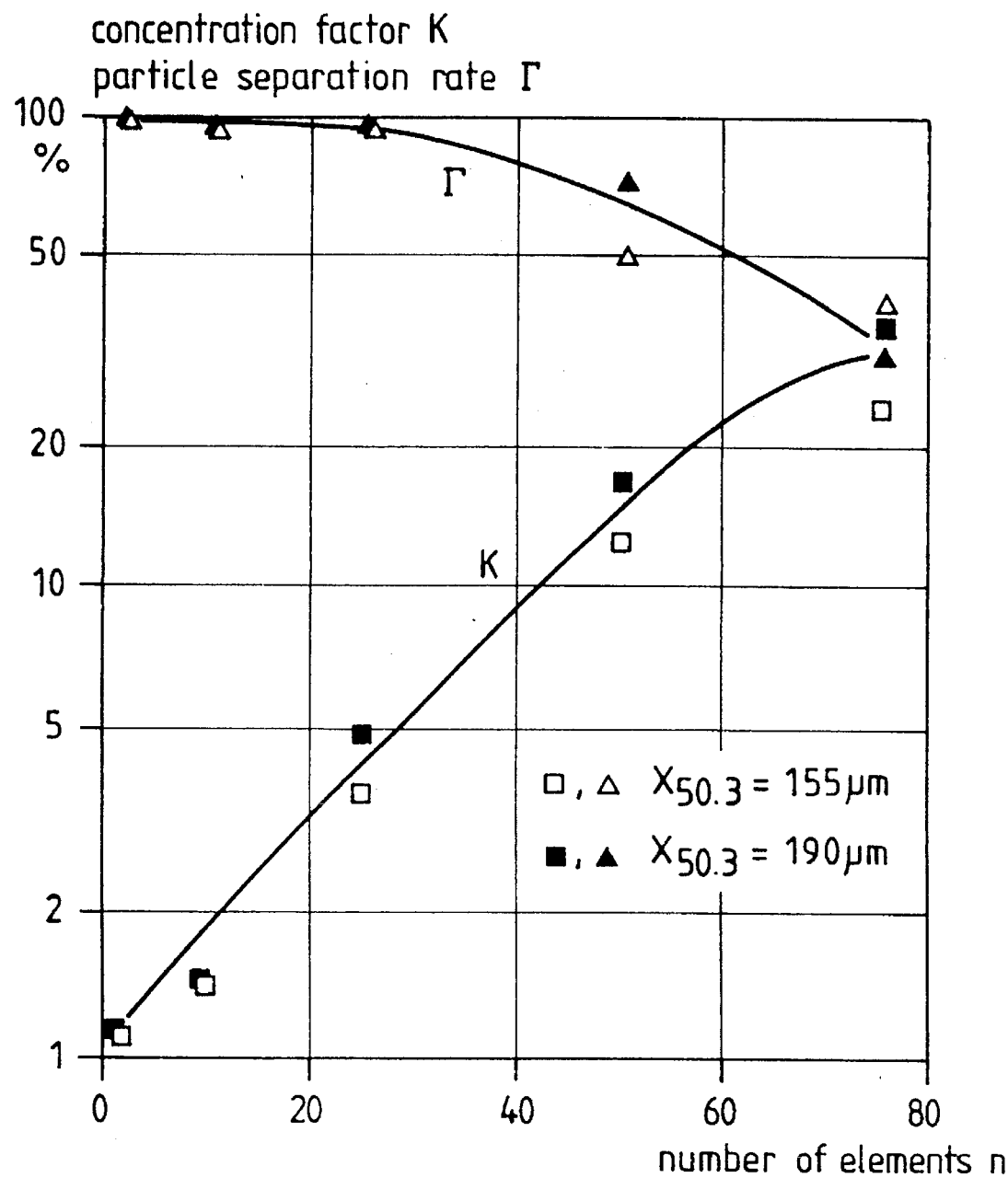

The invention will be described below in greater detail with the aid of embodiments and drawings, in which:

FIG. 1 shows a concentrator stage with flow arrows to illustrate the physical mode of operation, FIG. 2 shows a cross-section through the concentrator stage according to FIG. 1, FIG. 3 shows a stream concentrator with several concentrator stages connected behind each other in the form of a cascade, FIG. 4 shows the particle penetration fraction as a function of a standardized particle size with experimentally determined and theoretically calculated curves, FIG. 5 shows the total concentrate fraction in a multi-stage stream concentrator as a function of the number of concentrator stages and FIG. 6 shows the concentration factor and/or degree of particle separation in the examination of spherical particles in a liquid with identical density as a function of the number of stages.

The separation principle of the stream concentrator is based on the discharge of a particle-free zone close to the wall from a suspension stream flowing through a narrow channel. The channel can be a gap with flat boundary surfaces or as shown in FIG. 1, a capillary 1 with circular cross-section. In this case the separation stage comprises four separation pipes 2 attached to the capillary 1 at an angle of 135° and evenly distributed over the periphery. Ideally, the separation pipes 2 are replaced by a funnel-shaped separation channel which adjoins an annular gap in the capillary.

The separation effect is based on the fact that compared to the feed stream conveyed through the capillary 1, the particle concentration in the main stream flowing on through the capillary 1 is enriched and is diluted in the partial streams drawn off through the separation pipes 2.

As shown in FIG. 1, the boundary flow lines 3 divide the core stream flowing straight on from the laterally drawn off boundary layer stream. A purely geometrical blocking effect rules out the possibility of particles 4, whose radius exceeds the thickness $x_T = \frac{1}{2}(D - D_k)$ of the boundary layer, finding their way into the discharged liquid. This also applies to deformable particles which are kept in the core stream by means of flow forces.

Smaller particles whose radius is less than the thickness of the boundary layer are no longer completely retained but in only a fraction which decreases as the ratio of particle radius to boundary layer radius decreases.

With a single separation stage, as shown in FIGS. 1 and 2, only a limited degree of liquid separation and hence a limited concentration factor can be achieved. For a design with a diameter $D=1$ mm and four separation pipes 2 with holes of 0.6 mm diameter arranged on the periphery at an angle of 135°, for example, an elementary degree of liquid separation $\lambda$ of 5% to 6% was obtained with a free outflow from liquid and concentrate openings. With four openings of 0.6 mm diameter the total cross-section is 1.44 times the cross-section of the capillary of 1 mm diameter. The elementary degree of liquid separation is defined as the ratio of outflow $\Delta\dot{V}$ of the particle-depleted liquid close to the wall to the inflow $\dot{V}$:

$$\lambda = \frac{\Delta\dot{V}}{\dot{V}}$$

The inflow $\dot{V}$ is set with a pump. The elementary degree of liquid separation $\lambda$ can of course be reduced or increased by throttling the outflow on the liquid side and/or the concentrate side.

The elementary concentration factor $\kappa$ is defined as the ratio of the particle concentration $C+\Delta C$ in the concentrate outflow to the particle concentration $C$ in the inflow:

$$\kappa = \frac{C + \Delta C}{C}$$

For technical tasks, an elementary degree of liquid separation of 5% to 6% and a consequent elementary concentration factor in the case of full separation of approx. 1.05 to 1.06 is not usually adequate. This is why several concentrator stages 5 according to FIG. 3 are connected behind each other in the form of a cascade for technical application.

The stream concentrator comprising n separation stages divides the feed suspension 6 with the throughput $V_A$ and the particle concentration $C_A$ into a concentrate 7 and a liquid 8 (ideally particle-free). The function of the stream concentrator of n stages is identified by the concentration factor $K=C_K/C_A$ which is obtained as the nth power of the elementary concentration factor and by concentrate fraction and/or degree of liquid separation which are obtained from powers of the complement to the elementary degree of liquid separation.

In all, a concentration factor $$K = \kappa^n,$$

a concentrate fraction $$\dot{V}_K/\dot{V}_A = (1-\lambda)^n$$

and a degree of liquid separation $$\dot{V}_L/\dot{V}_A = 1-(1-\lambda)^n$$

are obtained.

A stream concentrator with n separation stages $5_n$ is achieved by means of n successive hole systems in the direction of flow. Designs with up to 75 elements were tested, for example; the pipe diameter D varied between 1 and 2 mm. Throughputs between 100 and 500 l/hr were achieved with pressures of 10 bars for example. The partial streams drawn off in the individual separation stages $5_n$ are discharged through the collective shaft 9 and the outlet 10.

Substantially higher throughputs can be achieved in the design with a flat channel gap. This also applies to rotationally symmetrical designs with a larger pipe diameter D. On the other hand, for a particular elementary degree of liquid separation, the particle size limit $X_T$ is in a particular ratio to the pipe diameter D. Complete separation can no longer be assured with smaller ratios X/D.

FIG. 4 shows the particle penetration fraction, defined as concentration $C_L$ in the discharged liquid related to the concentration $C_A$ in the feed as a function of the related particle size X/D. The curves calculated for turbulent flow at Reynolds numbers between $10^4$ and $10^5$ relate to ideal ring discharge with elementary degrees of liquid separation $\lambda$ between 2% and 30%. With an elementary degree of separation of 5%, a separation grain size of 3% of the pipe diameter D is theoretically obtained, for example, because of the blocking effect. If the separation grain size is not reached the particle penetration fraction rises steeply. The curves marked a, b and c relate to calculated values, the basis of which was the not ideal discharge through 4 separation pipes. In the illustration of the corresponding experimental results with spherical particles the median value of the actual particle size distribution was involved in the definition of X/D. Flatter curves than were calculated are obtained because of the fines content of the distribution.

With free outflow from liquid and concentrate side the elementary degree of liquid separation λ of the stream concentrator designs tested is approximately 5% to 6%. λ can be increased by throttling on the concentrate side.

For the operation of the stream concentrator without throttling FIG. 5 shows the total concentrate fraction and/or the total degree of liquid separation as a function of the number n of separation stages. The particles were spherical. Their density was the same as the liquid density. The median values $X_{50.3}$ of the two particle size distributions examined were 155 μm and 190 μm. With n=25 stages a degree of liquid separation of 75% was achieved; with 50 and 75 stages a degree of liquid separation of 95 and 99% was already achieved.

FIG. 6 shows the concentration factor K achieved with the same experiments with spherical particles in liquid of identical density. A concentration by the factor 30 was achieved with n=75 elements. In the example illustrated the particle volume concentration was increased from 0.5% to 15%. Systematic experiments which varied the feed concentration have shown that concentration factor and degree of separation are independent of concentration up to final volume concentrations of 30%. This limit is determined solely by the restricted flowability of highly concentrated suspensions.

The degree of particle separation Γ does, however, reduce at high degrees of liquid separation and correspondingly low concentrate fractions because of the low flow rate of the main stream and the changeover from turbulent to laminar flow. Virtually complete particle separation was still assured with n=25 elements and concentration factors around 4. If virtually complete particle separation is also required at higher concentration factors, concentration in several stages by the factor 4 in each case, for example, is suitable. The stream concentrator according to the invention thus makes available a simple system for concentrating suspensions which can be applied both with imperceptible density difference, with which sedimentation methods fail, and with deformable particles, where cake or cross-flow filtration methods fail.

The stream concentrator solves the problem of concentrating particles even when they are deformable and do not differ from the liquid in terms of density. The achievable final concentration is only restricted by the limit of the flowability of the suspension. The achievable volume concentration can, therefore, be up to 60% depending on the substance system. The feed concentration is preferably in the range from 0.1 to 10%.

A single-stage concentration is adequate or a multi-stage concentration is required depending on the requirements regarding the degree of particle separation. With the multi-stage method, particle volume concentrations under 0.1% in the liquid to be discharged can be achieved with the stream concentrator.

The experimental results reported as an example were determined on a number of specific embodiments of the stream concentrator according to the invention.

The dimensions of the main stream channel must definitely exceed the diameter of the largest particles in the dispersion. The dimensions of the liquid discharge channels as well as the number of elements connected behind each other in the form of a cascade should be adapted to the partition ratio determined by the separation task and the permissible particle content in the liquid outlet and the fines content of the particle size distribution of the dispersion. The experimental and theoretical results which are reported are of use in this.

Main channel dimensions of approx. 20 μm to approx. 10 mm come into question in the application to separate microgel particles or macroscopic gel particles from polymer solutions with particle sizes of approx. 10 μm to approx. 1 mm for example.

Main channel dimensions down to below 10 μm are suitable in the application in biotechnology for separating microorganisms, e.g. bacteria of approx. 1 μm diameter. Main channel dimensions down to below 1 μm can be involved for the separation of cell fragments following mechanical cell breakdown. With the modern methods of manufacture of microstructure technology, the requirements for the manufacture of stream concentrators with fine structures of this kind exist today and can also be used for technical application.

The angle of the discharge channels with respect to the pipe axis should be as obtuse as possible, so as to be able to make use of an additional inertia effect in the separation in the case of particles of higher density. In this case the angle should be at least 90° Angles above 170° are problematic for reasons of geometry and production technology.

As outlined in FIG. 1, the liquid discharge channels can be incorporated in the form of holes in a pipe or a channel of another shape.

The system can, however, also be composed of a set of annular elements between which gaps can be produced, by means of spacers for example.

Furthermore, the diameter or the channel width of the main stream channel of a multi-stage stream concentrator need not be constant. The channel cross-section can, for example, be reduced downstream to the extent to which liquid has already been drawn off. The mean flow rate remains constant because of this measure. Nor, as in FIG. 3 in the case of a multistage stream concentrator, do the liquid streams of all n stages need to be combined. Rather, several, and all n elements as a maximum, can be connected to separate liquid take-off lines. The result of this is that separate liquid fractions with different particle content if necessary are not combined again. As the particle fractions discharged with the separate liquid take-off lines also differ in the mean particle size, in this embodiment the stream concentrator is also suitable for grading.

An important example of the application of the stream concentrator is the separation of microgel particles from polymer solutions and melts. Such microgel particles cause serious quality losses because, for example, of optical non-uniformities, or breakdowns such as torn fibers in the spinning process. Among other things, problems with microgel separation arise through the low density difference with respect to the surrounding liquid and through the deformability of these particles.

Similar requirements—low density difference and deformability—also exist for various tasks in biotechnology. The stream concentrator is suitable for concentrating microorganisms such as bacteria, yeasts or moulds. In principle, cell fragments can also be concentrated if modern methods of microstructure technology are used to produce channels with diameters and/or widths in the μm order of magnitude.

The stream concentrator is also suitable for concentrating emulsions (oil-in-water or water-in-oil emulsions) and for separating aqueous two-phase systems.

The stream concentrator is suitable not only as a continuous separation step following a chemical or physical reaction process but can also be integrated into reaction processes particularly easily. This means that reactions can be carried out more selectively, if, for example, desired reaction products which can react further to produce undesired derived products are discharged from the process.

I claim:

1. Method for concentrating suspended particles in a liquid, wherein the suspension is made to flow as the feed stream through a narrow channel or a capillary having a channel width or capillary diameter of from 0.5 µm to 10 mm and partial streams are drawn off from the wall on the periphery of the channel or the capillary through openings in the channel wall or capillary wall, the cross-section of which is larger than the mean particle cross-section, wherein a liquid boundary layer is formed in the proximity of the walls and the particle concentration is enriched in the main stream and diluted in the partial streams compared to the feed stream not by the action of centrifugal forces in the main stream, but by a geometrical blocking effect which prevents particles having a radius which is larger than the thickness of the boundary layer from entering the openings in the channel or capillary walls.

2. Method according to claim 1, wherein the partial stream close to the wall is drawn off with a direction component against the main stream, with a deviation angle between 120° and 150°.

3. Method according to claim 1, wherein turbulent flow conditions prevail in the main stream.

4. Method according to claim 1, wherein laminar flow conditions are present in the partial streams.

5. Method according to claim 1, wherein the partial stream from the openings at identical axial height is 2% to 10% of the main stream.

6. Method according to claim 1, wherein partial streams are drawn off successively in the form of a cascade in the direction of flow.

7. Method according to claim 6, wherein the partial streams drawn off from different axial heights are discharged separately in order to obtain partial streams of different particle concentration and different particle size distribution.

8. Method according to claim 6, wherein the sum of all partial streams is 75% to 99% of the feed stream.

9. Method according to claim 1, wherein particle and liquid are separated from each other in the course of an on-going chemical reaction.

10. Device for implementing the method according to claim 1, wherein several holes with diameters between 10% and 90% of the pipe diameter are arranged at identical axial height on the periphery of a pipe in which the main stream is conveyed.

11. Device for implementing the method according to claim 1, wherein two gaps with gap widths between 5% and 50% of the channel width are arranged at identical axial height on opposite walls of a flat channel with rectangular cross-section, in which the main stream is conveyed.

12. Device for implementing the method according to claim 1, wherein the holes or gaps for drawing off the particle-depleted partial streams have dimensions of 1 to 10 times the median value of the particle size distribution of the feed stream.

13. Device according to claim 10, wherein several such hole and/or gap systems are arranged behind each other in the form of a cascade in the direction of flow.

14. Device according to claim 10, wherein the total cross-section of the openings at identical axial height is 0.5 to 4 times the channel and/or capillary cross-section.

* * * * *